United States Patent
Scholey et al.

(10) Patent No.: US 9,956,241 B2
(45) Date of Patent: *May 1, 2018

(54) APPLICATION OF AMERICAN GINSENG TO ENHANCE NEUROCOGNITIVE FUNCTION

(71) Applicant: NATUREX, S.A., Avignon (FR)

(72) Inventors: Andrew Scholey, Hawthorn (AU); Alvin Ibarra, Helsinki (FI); Kan He, River Edge, NJ (US); Marc Roller, Moriéres-lés-Avignon (FR); Jacques Dikansky, Avignon (FR)

(73) Assignee: Naturex, S.A., Avignon (FR)

( * ) Notice: Subject to any disclaimer, the term of this patent is extended or adjusted under 35 U.S.C. 154(b) by 269 days.

This patent is subject to a terminal disclaimer.

(21) Appl. No.: 14/633,168

(22) Filed: Feb. 27, 2015

(65) Prior Publication Data
US 2015/0306119 A1 Oct. 29, 2015

Related U.S. Application Data

(60) Continuation-in-part of application No. 13/288,745, filed on Nov. 3, 2011, now Pat. No. 8,968,800, which is a division of application No. 12/435,343, filed on May 4, 2009, now abandoned.

(51) Int. Cl.
*A61K 31/704* (2006.01)
*A61K 36/258* (2006.01)

(52) U.S. Cl.
CPC .......... *A61K 31/704* (2013.01); *A61K 36/258* (2013.01)

(58) Field of Classification Search
None
See application file for complete search history.

(56) References Cited

U.S. PATENT DOCUMENTS

| | | | |
|---|---|---|---|
| 6,083,932 A | 7/2000 | Pang et al. | |
| 6,156,291 A | 12/2000 | Pang et al. | |
| 6,773,729 B2 | 8/2004 | Petrini et al. | |
| 7,585,525 B2 | 9/2009 | Park | |
| 8,968,800 B2 * | 3/2015 | Scholey | A61K 36/258 424/728 |
| 2002/0015744 A1 | 2/2002 | Petrini et al. | |
| 2003/0064118 A1 | 4/2003 | Petrini et al. | |
| 2005/0031711 A1 | 2/2005 | Park | |
| 2005/0233004 A1 | 10/2005 | Shin et al. | |
| 2006/0257502 A1 | 11/2006 | Liu | |
| 2007/0031568 A1 | 2/2007 | Gardiner et al. | |
| 2007/0036873 A1 | 2/2007 | Ghosal | |
| 2007/0167509 A1 | 7/2007 | Araujo et al. | |
| 2007/0184129 A1 | 8/2007 | Woo et al. | |
| 2007/0281010 A1 | 12/2007 | Reynolds | |
| 2007/0281961 A1 | 12/2007 | Reynolds | |
| 2008/0085888 A1 | 4/2008 | Breining et al. | |
| 2008/0213401 A1 | 9/2008 | Smith | |
| 2008/0227760 A1 | 9/2008 | Li | |
| 2008/0312187 A1 | 12/2008 | Kim et al. | |

FOREIGN PATENT DOCUMENTS

| | | |
|---|---|---|
| CN | 1457793 A * | 11/2003 |
| WO | 2007035723 A2 | 3/2007 |

OTHER PUBLICATIONS

F. Sala et al., Effects of ginsenoside Rg2 on human neuronal nicotinic acetylcholine receptors, The Journal of Pharmacology and Experimental Therapeutics, Jun. 2002, pp. 1052-1059, vol. 301, issue 3, The American Society for Pharmacology and Experimental Therapeutics, United States.
R. Lewis et al., Non-ginsenoside nicotinic activity in *Ginseng* species, Phytother. Res., Feb. 1999, pp. 59-64, vol. 13, issue 1, John Wiley & Sons, Ltd., United States.
V. Vuksan et al., American ginseng (*Panax quinquefolius* L) reduces postprandial glycemia in nondiabetic subjects and subjects with type 2 diabetes mellitus, Arch. Intern. Med., Apr. 10, 2000, pp. 1009-1013, vol. 160, issue 7, American Medical Assn., United States.
Y. Oshima et al., Isolation and hypoglycemic activity of quinquefolans A, B, and C, glycans of *Panax quinquefolium* roots, Journal of Natural Products, 1987, pp. 188-190, vol. 50, issue 2, American Society of Pharmacognosy, United States.
B. Martinez et al., The physiological effects of Aralia, Panax and Eleutherococcus on exercised rats, Japan. J. Pharrnacol., Jun. 1984, pp. 79-85, vol. 35, issue 2, Japanese Pharmacological Society, Japan.
V. Buksan et al., Similar postprandial glycemic reductions with escalation of dose and administration time of American ginseng in type 2 diabetes, Diabetes Care, Sep. 2000, pp. 1221-1226, vol. 23, No. 9, American Diabetes Association, United States.
V. Vuksan et al., Korean red ginseng (Panax ginseng) improves glucose and insulin regulation in well-controlled, type 2 diabetes: results of a randomized, double-blind, placebo-controlled study of efficacy and safety, Nutrition Metabolism & Cardiovascular Diseases., Jan 2008, pp. 46-56, vol. 18, issue 1, Elsevier, Netherlands.
E. Reich et al., Validation of High-Performance Thin-Layer Chromatographic Methods for the Identification of Botanicals in a cGMP Environment, Journal of AOAC International, Jan. 2008, pp. 13-20, vol. 91, issue 1, AOAC International, United States.
J. M. Durgnat et al., Quality and safety assessment of ginseng extracts by determination of the contents of pesticides and metals, Food Additives and Contaminants, Dec. 2005, pp. 1224-1230, vol. 22, issue 12, Taylor & Francis Group, United Kingdom.
M. R. Harkey et al., Variability in commercial ginseng products: an analysis of 25 preparations, Am. J. Clin. Nutr., Jun. 2001, pp. 1101-1106, vol. 73, issue 6, American Society of Clinical Nutrition, United States.

(Continued)

*Primary Examiner* — Susan Hoffman
(74) *Attorney, Agent, or Firm* — LeClairRyan PLLC

(57) ABSTRACT

Disclosed are methods of enhancing neurocognitive function by administering of American *Ginseng*. Preferred dosages in the range of 5 to 50 mg total ginsenosides enhance cognitive function—including, improvement of working memory (WM) performance, attentional performance (e.g., Choice Reaction Time accuracy), and calmness.

8 Claims, 2 Drawing Sheets

(56) References Cited

OTHER PUBLICATIONS

T. C. Wen et al., Ginseng root prevents learning disability and neuronal loss in gerbils with 5-minute forebrain ischemia, Acta Neuropathol, 1996, pp. 15-22, vol. 91, issue 1, Springer-Verlag, Germany.
R. Z. Zhao et al., Ginseng improves strategic learning by normal and brain-damaged rats, NeuroReport, Nov. 11, 1998, pp. 1619-1624, vol. 9, issue 7, Lippincott Williams & Wilkins, United Kingdom.
H. Nitta et al., Panax ginseng extract improves the scopolamine-induced disruption of 8-arm maze performance in rats, Biol. Pharm. Bull., Nov. 1995, pp. 1439-1442, vol. 18, issue 10, Pharamceutical Society of Japan, Japan.
V. D. Petkov et al., Effects of standardized ginseng extract on learning, memory and physical capabilities, American Journal of Chinese Medicine, Feb. 1987, pp. 19-29, vol. 15, Nos. 1-2, World Scientific, Singapore.
V. D. Petkov et al., Memory effects of standardized extracts of Panax ginseng (G115), Ginkgo biloba (GK501) and their combination Gincosan® (PHL-00701), Planta Med., Apr. 1993, pp. 106-114, vol. 59, issue 2, Thieme Medical Publishers, Germany.
M. Neri et al., Influence of a double blind pharmacological trial on two domains of well-being in subjects with age associated memory impairment, Archives of Gerontology and Geriatrics, 1995, pp. 241-252, vol. 21, issue 3, Elsevier, Netherlands.
E. A. Sotaniemi et al., Ginseng therapy in non-insulin-dependent diabetic patients, Diabetes Care, Oct. 1995, pp. 1373-1375, vol. 18, No. 10, American Diabetes Association, United States.
B. Thommenssen et al., No identifiable effect of ginseng (Gericomplex) as an adjuvant in the treatment of geriatric patients, Aging Clin. Exp. Res., Dec. 1996, pp. 417-420, vol. 8, No. 6, Editrice Kurtis S.R.L., Italy.
H. Sørensen et al., A double-masked study of the effects of ginseng on cognitive functions, Current Therapeutic Research, Dec. 1996, pp. 959-968, vol. 57, No. 12, Elsevier, Netherlands.
L. D'Angelo et al., A double-blind, placebo-controlled clinical study on the effect of a standardized ginseng extract on psychomotor performance in healthy volunteers, Journal of Ethnopharmacology, Apr. 1986, pp. 15-22, vol. 16, issue 1, Elsevier Scientific Publishers Ireland Ltd., Ireland.
M. S. Bahrke et al., Evaluation of the ergogenic properties of ginseng, Am. J. Sports Med., Oct. 1994, pp. 229-248, vol. 18, issue 4, Springer International, New Zealand.
M. S. Bahrke et al., Evaluation of the ergogenic properties of ginseng: An update, Am. J. Sports Med., Mar. 2000, pp. 113-133, vol. 29, issue 2, Springer International, New Zealand.
D. O. Kennedy et al., Modulation of mood and cognitive performance following acute administration of single doses of *Melissa officinalis* (Lemon balm) with human CNS nicotinic and muscarinic receptor-binding properties, Neuropsychopharmacology., Oct. 2003, pp. 1871-1881, vol. 28, issue 10, Nature Publishing Group, United Kingdom.
A. B. Scholey et al., Acute, dose-dependent cognitive effects of Ginkgo biloba, Panax ginseng and their combination in healthy young volunteers: differential interactions with cognitive demand, Human Psychopharmacology, Jan. 2002, pp. 35-44, vol. 17, issue 1, John Wiley & Sons, Ltd., United Kingdom.
D. O. Kennedy et al., Dose dependent changes in cognitive performance and mood following acute administration of Ginseng to healthy young volunteers, Nutritional Neuroscience, 2001, pp. 295-310, vol. 4, issue 4, Maney Publishing, United Kingdom.
D. O. Kennedy et al., Differential, dose dependent changes in cognitive performance following acute administration of a Ginkgo biloba/Panax ginseng combination to healthy young volunteers, Nutritional Neuroscience, Feb. 2001, pp. 399-412, vol. 4, issue 5, Maney Publishing, United Kingdom.
D. O. Kennedy et al., Modulation of cognition and mood following administration of single doses of Ginkgo biloba, Ginseng and a Ginkgo/Ginseng combination to healthy young adults, Physiology & Behavior, Apr. 15, 2002, pp. 739-751, vol. 75, issue 5, Elsevier, Netherlands.
J. L. Reay et al., Single doses of Panax ginseng (G115) reduce blood glucose levels and improve cognitive performance during sustained mental activity, Journal of Psychopharmacology, Jul. 2005, pp. 357-365, vol. 19, issue 4, SAGE Publications Ltd., United Kingdom.
J. L. Reay et al., Effects of Panax ginseng, consumed with and without glucose, on blood glucose levels and cognitive performance during sustained 'mentally demanding' tasks, Journal of Psychopharmacology, Dec. 2006, pp. 771-781, vol. 20, issue 6, SAGE Publications Ltd., United Kingdom.
C. G. Benishin et al., Effects of ginsenoside Rb1 on central cholinergic metabolism, Pharmacology., 1991, pp. 223-229, vol. 42, issue 4, S. Karger AG, Switzerland.
C. G. Benishin, Action of ginsenoside Rb1 on choline uptake in central cholinergic nerve endings, Neurochem. Int., Jul. 1992, pp. 1-5, vol. 21, No. 1, Pergamon Press Ltd., United Kingdom.
J. T. Zhang et al., Preliminary study on antiamnestic mechanism of ginsenoside Rg1 and Rb1, Chinese Medical Journal, Nov. 1990, pp. 932-938, vol. 103, issue 11, Chinese Medical Association and Pergamon Press, China.
K. N. Salim et al., Ginsenoside Rb1 regulates ChAT, NGF and trkA mRNA expression in the rat brain, Molecular Brain Research, Aug. 1997, pp. 177-182, vol. 47, issue 1-2, Elsevier, Netherlands.
S. Hiai et al., Evaluation of corticosterone secretion-inducing activities of ginsenosides and their prosapogenins and sapogenins, Chem. Pharm. Bull., Feb. 1983, pp. 168-174, vol. 31, issue 1, Pharmaceutical Society of Japan, Japan.
D. Tsang et al., Ginseng saponins: Influence on neurotransmitter uptake in rat brain synaptosomes, Planta Medica, Jul. 1985, pp. 221-224, vol. 51, issue 3, Thieme Medical Publishers, Germany.
K. Abe et al., Differential effects of ginsenoside Rb1 and malonylginsenoside Rb1 on long-term potentiation in the dentate gyrus of rats, Brain Research, Jul. 1994, pp. 7-11, vol. 649, issue 1-2, Elsevier, Netherlands.
B. D. Sloley et al., American ginseng extract reduces scopolamine-induced amnesia in a spatial learning task, J Psychiatry Neurosci., Nov. 1999, pp. 442-452, vol. 24, issue 5, Canadian Medical Association, Canada.
D. Seely, Safety and efficacy of Panax ginseng during pregnancy and lactation, Can. J. Clin. Pharmacol., Feb. 2008, pp. 87-94, vol. 15, issue 1, Canadian Society of Pharmacology and Therapeutics, Canada.
Brahmi herb shows promise in treating Alzheimer's, Thaindian News, Dec. 6, 2009, Thailand, [online], <URL: http://www.thaindian.com/newsportal/health1/brahmi-herb-shows-promise-in-treating-alzheimers_100284982.html>.
Supplier's Corner: Cereboost, Nutraceuticals World, Dec. 1, 2009, United States, [online], <URL: http://www.nutraceuticalsworld.com/issues/2009-12/view_suppliers-corner/cereboost/>.
Yojana Sharma, Pills and notions Brain-enhancing pills are becoming popular among students, China Morning Post, Feb. 7, 2009, China.
Sean Moloughney, Keys to cognitive health, Nutriceuticals World, Oct. 1, 2008, United States, [online], <URL: http://www.nutraceuticalsworld.com/issues/2008-10/view_features/keys-to-cognitive-health>.
Medicine: Smart drugs, The Economist, May 22, 2008, United Kingdom, [online], <URL: http://www.economist.com/node/11412603>.
Potter's goes on acquisition trail, Nutraceuticals International, Nov. 1, 2005, Marketletter Publications Ltd., United Kingdom.
S. Henderson, It's all too easy to forget, Mar. 29, 2004, The Independent, United Kingdom, [online], <URL: http://www.independent.co.uk/lifestyle/healthandfamilies/healthnews/itsalltooeasytoforget568072.html>.
S. Janes, Brain boosters; Can chewing gum really improve your memory?, Jun. 13, 2002, The Mirror, United Kingdom.
K. Bone, Ginkgo and Korean Ginseng Combined Boost Brainpower, Townsend Letter for Doctors and Patients, Jun. 1, 2002, pp. 92, vol. 227, Jonathan Collin, United States.

(56) References Cited

OTHER PUBLICATIONS

H. R. Lieberman, The effects of ginseng, ephedrine, and caffeine on cognitive performance, mood and energy, Nutrition Reviews, Apr. 2001, pp. 91-102, vol. 59, issue 4, International Life Sciences Institute, United States.

J. D. Churchill et al., The nootropic properties of ginseng saponin Rb1 are linked to effects on anxiety, Integrative Physiological & Behavioral Science, 2002, pp. 178-187, vol. 37, issue 3, Transaction Periodicals Consortium, United States.

A. Shergill, Ginseng and Memory, Nutrition Bytes, vol. 4, issue 2, 1998, University of California, United States, [online], <URL: http://escholarship.org/uc/item/7sn5s2h5>.

Cognitive, Emotional, Physical and Psychosocial Effects of Panax Quinquefolius L (REMEMBER-fX), Mar. 2008, ClinicalTrials.gov. United States, [online], <URL: https://clinicaltrials.gov/ct2/show/study/NCT00527969?term=Cognitive%2C+Emotional%2C+Physical+and+Psychosocial+Effects+of+Panax+Quinquefolius+L&rank=1>.

J. V. D. Borne, American Ginseng, Jake's Anxiety and Depression Solutions, [online], <URL: http://www.anxiety-and-depression-solutions.com/american-ginseng-137>, accessed Aug. 2015.

C. Z. Wang, Saponins composition in American ginseng leaf and berry assayed by high-performance liquid chromatography, Journal of Agricultural and Food Chemistry, Mar. 22, 2006, pp. 2261-2266, vol. 54, issue 6, American Chemical Society, United States.

M. R. Lyon et al., Effect of the herbal extract combination Panax quinquefolium and Ginkgo biloba on attention-deficit hyperactivity disorder: a pilot study, J. Psychiatry Neurosci., May 2001, pp. 221-228, vol. 26, issue 3, Canadian Medical Association, Canada.

H. Zhao et al., Long-term ginsenoside administration prevents memory impairment in aged C57BL/6J mice by up-regulating the synaptic plasticity-related proteins in hippocampus, Behavioural Brain Research, Aug. 12, 2009, pp. 311-317, vol. 201, issue 2, Elsevier, Netherlands.

Dr. W. Gifford Jones,. REMEMBER-fX: The Smart Pill, Canada Free Press, Jan. 11, 2005, Canada, [online], <URL: http://canadafreepress.com/medical/psychiatry011105.htm>.

H. S. Kim et al., Effects of ginsenosides on Ca2+ channels and membrane capacitance in rat adrenal chromaffin cells, Brain Research Bulletin, 1998, pp. 245-251, vol. 46, Issue 3, Elsevier Science Inc., United States.

J. D. E. Gabrieli et al., The role of left prefrontal cortex in language and memory, Proc. Natl. Acad. Sci. USA., Feb. 3, 1998, pp. 906-913, vol. 95, issue 3, National Academy of Sciences, United States.

P. S. Goldman-Rakic, The prefrontal landscape: implications of functional architecture for understanding human mentation and the central executive, Phil. Trans. R. Soc. Lond. B, Oct. 29, 1996, pp. 1445-1453, vol. 351, issue 1346, Royal Society, United Kingdom.

M. G. Giovannini et al., Differential regulation by N-methyl-D-aspartate and non-N-methyl-D-aspartate receptors of acetylcholine release from the rat striatum in vivo, Neuroscience, Mar. 1995, pp. 409-415, vol. 65, issue 2, Elsevier Science Ltd., United Kingdom.

\* cited by examiner

APPLICATION OF AMERICAN GINSENG TO ENHANCE NEUROCOGNITIVE FUNCTION

CROSS-REFERENCE TO RELATED APPLICATIONS

The present application is a continuation-in-part of U.S. application Ser. No. 13/288,745, filed on Nov. 3, 2011, now U.S. Pat. No. 8,968,800, which is a divisional of U.S. application Ser. No. 12/435,343, filed on May 4, 2009, now abandoned. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The present invention relates to the use of American Ginseng (*Panax quinquefolius*) to increase neurocognitive function (for example, memory, attention, and calmness, among others).

Description of the Related Art

The term "*Ginseng*" is generally used to refer to the species of the genus *Panax* of the family Araliaceae. Extracts of Asian *Ginseng* (*Panax ginseng*) have been used for millennia in Traditional Chinese Medicine for the prevention and treatment of a variety of diseases, and have been also used as general health elixirs and performance enhancers (including in the neurocognitive area). There is a growing body of evidence to support Asian *Ginseng* as a cognitive enhancer. American *Ginseng* (*Panax quinquefolius*) is also in the family Araliaceae, although until now the cognition-enhancing properties of American *Ginseng* have not been known.

Research evaluating behavioural effects of chronic administration of Asian *Ginseng* in animals has demonstrated attenuation of learning deficits in aged rodents (Wen, T. C. et al. (1996) "*Ginseng* root prevents learning disability and neuronal loss in gerbils with 5-minute forebrain ischemia," *Acta Neuropathol* 91:15-22; Zhao, R. & McDaniel, K. (1998) "*Ginseng* improves strategic learning by normal and brain-damaged rats," *NeuroReport* 9:1619-1624; Nitta, H. et al. (1995) "*Panax Ginseng* extract improves the scopolamine-induced disruption of 8-arm radial maze performance in rats" *Biol Pharm Bull* 18:1439-1442). In one study, not only was learning improved in gerbils with learning deficits associated with forebrain ischemia, but Asian *Ginseng* was also neuroprotective, rescuing hippocampal CA1 pyramidal neurons (Wen et al. 1996). In young rodents, Asian *Ginseng*-related improvements may follow an inverted U-dose response. Mice administered 3, 10, 30, 100 & 300 mg/kg Asian (extract G115) improved performance following 10 mg/kg in an inverted-U-dose-response manner. However, this effect was observed for a selection of tasks only (Petkov, V. D. & Mosharrof, A. H. (1987) "Effects of standardized *Ginseng* extract on learning, memory and physical capabilities," *Am J Chin Med* 15:19-29). Studies have observed cognitive benefits over a range of dosages of Asian *Ginseng*, ranging from 10 mg/kg to 150 mg/kg (Petkov & Mosharrof, 1987; Petkov V. D. et al. (1993) "Memory effects of standardized extracts of *Panax Ginseng* (G115), *Ginkgo biloba* (GK 501) and their combination Gincosan (PHL-00701)," *Planta Med* 59:106-114), with some doses appearing to impair cognitive function. For example, Petkov & Mosharrof (1987) found that higher dosages of Asian *Ginseng* G115 (300 mg/kg) impaired conditioned reflex activity in rats. The dose-response profile of Asian *Ginseng* is further complicated by variations in methods of assessment, age and dosage (Petkov et al. 1993).

In the few chronic administration studies on human subjects beneficial effects of Asian *Ginseng* were observed in cognitive deficit populations. For example, Neri et al. administered an Asian *Ginseng*-containing vitamin complex or placebo for 9 months and examined performance of participants suffering from age-related cognitive decline (Neri, M. et al. (1995) "Influence of a double blind pharmacological trial on two domains of well being in subjects with age associated memory impairment," *Arch Gerontol Geriatr* 21:241-252). They observed improvement of mnemonic performance following Asian *Ginseng*. In non-insulin dependent diabetic patients 8-week administration of 200 mg Asian *Ginseng* improved psychophysical performance compared to placebo (Sotaniemi, E. A. et al. (1995) "*Ginseng* therapy in non-insulin-dependent diabetic patients," *Diabetes Care* 18:1373-1375). One study aimed to assess the effects of an Asian *Ginseng* supplement combination 'Gericomplex' (Asian *Ginseng*, vitamins, minerals and trace elements) on mental health and wellbeing of geriatric patients. Two capsules were taken daily for 8 weeks, but they failed to observe any cognitive enhancement by the intervention (Thommessen, B. & Laake, K. (1996) "No identifiable effect of *Ginseng* (Gericomplex) as an adjuvant in the treatment of geriatric patients," *Aging* 8:417-420). In healthy individuals over the age of 40 Sorensen & Sonne administered 400 mg of standardized Asian *Ginseng* extract for 8 to 9 weeks and observed significantly faster reaction times compared to placebo (Sorensen, H. & Sonne, J. (1996) "A double masked study of the effects of *Ginseng* on cognitive functions," *Curr Ther Res* 57:959-968). In healthy young individuals D'Angelo et al. found that following 12 weeks of treatment of either 100 mg of Asian *Ginseng* (G115) or placebo (taken twice daily), patients administered Asian *Ginseng* demonstrated mental arithmetic (D'Angelo, L. et al. (1986) "A double-blind, placebo-controlled clinical study on the effect of a standardized *Ginseng* extract on psychomotor performance in healthy volunteers," *J Ethnopharmacol* 16:15-22). However, these data should be interpreted with caution as the above studies have been criticized on a number of methodological issues such as inadequate sample sizes, non-standardised treatments, and inadequate research designs and statistical analysis (see Bahrke, M. S. & Morgan, W. P. (1994) "Evaluation of the ergogenic properties of *Ginseng*," *Sports Med* 18:229-248; Bahrke, M. S. & Morgan, W. P. (2000) "Evaluation of the ergogenic properties of *Ginseng*: an update," *Sports Med* 298:113-133; Kennedy, D. O. et al. (2003) "Modulation of mood and cognitive performance following administration of single doses of *Melissa officinalis* (Lemon balm) with human CNS nicotinic and muscarinic receptor binding properties," *Neuropsychopharmacology* 28: 1871-1881).

In a series of studies assessing the effects of acute administration of Asian *Ginseng* on cognition in young healthy individuals, enhancement by Asian *Ginseng* was observed largely for 'secondary memory' (a composite of four secondary memory tasks). (Kennedy et al. 2003; Scholey, A. B. & Kennedy, D. O. (2002) "Acute, dose-dependent cognitive effects of *Ginkgo biloba, Panax ginseng* and their combination in healthy young volunteers: differential interactions with cognitive demand," *Hum Psychopharmacol Clin* 17:35-44). In the first study, doses of 200, 400 and 600 mg Asian *Ginseng* (G115) were administered (Kennedy, D. O., et al. (2001a) "Differential, dose-dependent changes in cognitive performance and mood following acute administration of *Ginseng* to healthy young volunteers," *Nutr Neurosci* 4:295-310). Enhancement of 'secondary memory' was found following 400 mg at four post-dose testing sessions, while the lower and higher dosage diminished performance for 'speed of attention' (Id.)

In a further study, assessing combinations of Asian *Ginseng* and *Ginkgo* (ratio 100:60) at dosages of 320, 640, 960 mg, a similar pattern was observed (Kennedy, D. O. et al. (2001b) "Differential, dose dependent changes in cognitive performance following acute administration of a *Ginkgo biloba/Panax Ginseng* combination to healthy young volunteers," *Nutr Neurosci* 4:399-412). With performance of secondary memory being improved by 960 mg, and reduced performance on speed of attention for the other dosages (320 and 640 mg) (Id.). A later study, replicated the finding that a 400 mg dosage improves "secondary memory." Further study also assessed the effect of 200, 400 and 600 mg Asian *Ginseng* on mental arithmetic performance, where cognitive demand was manipulated (Kennedy, D. O., et al. (2002a) "Modulation of cognition and mood following administration of single doses of *Ginkgo biloba*, *Ginseng* and a *Ginkgo/Ginseng* combination to healthy young adults," *Physiol Behav* 72:953-964). Again this task was improved by a 400 mg dosage but only for the most demanding version of the task (Serial Sevens) (Reay, J. L. et al. (2005) "Single doses of *Panax ginseng* (G115) reduce blood glucose levels and improve cognitive performance during sustained mental activity," *J Psychopharmacol.* 19(4):357-65; Reay, J. L. et al. (2006) "Effects of *Panax ginseng*, consumed with and without glucose, on blood glucose levels and cognitive performance during sustained 'mentally demanding' tasks," *J Psychopharmacol.* 20(6):771-81.) It appears to be the case that Asian *Ginseng* or its constituents are capable of producing tangible cognitive enhancing effects and that for Asian *Ginseng* 200 or 400 mg appears to be an optimal dose for young healthy adults when administered acutely prior to a cognitive test.

The constituents of Asian *Ginseng* (*Panax ginseng*) that are thought to contribute to its bioactivity are the ginsenoside saponins Ginsenosides can be classified into three groups on the basis of their chemical structure: the Panaxadiol group (Rb1, Rb2, Rb3, Rc etc.), Panaxatriol group (Re, Rf, Rg1, Rg2, Rh1), and the oleanolic acid group (e.g. Ro).

American *Ginseng* (*Panax quinquefolius*), by contrast, has its own characteristic profile exhibiting a high expression of the Ginsenoside Rb1. The American *Ginseng* extract used in the present study contains 11.65% Ginsenosides (Rb1 (5.68%), Re (2.05%), Rc (1.86%), Rd (1.47%), Rb2 (0.029%), Rg1 (0.027%)).

Many of these ginsenosides have been isolated and evaluated for pharmacological effects in animal and human models. They have been reported to exert effects on the cholinergic system; isolated Rb1 was both observed to increase synaptosomal choline uptake, and stimulate acetylcholine release (Benishin, C. G. et al. (1991) "Effects of ginsenoside Rb1 on central cholinergic metabolism," *Pharmacology* 42:223-229; Benishin, C. G. (1992) "Actions of ginsenoside Rb1 on choline uptake in central cholinergic nerve endings," *Neurochem. Int.* 21:1-5). Ginsenosides Rg1 and Rb1 have also been found to elicit marked alterations in brain serotonin concentrations (Zhang, J. T. et al. (1990) "Preliminary study on antiamnestic mechanism of ginsenoside Rg1 and Rb1," *Chin Med J* 103:932-938). Furthermore, Salim found that in rat brains Rb1 increased expression of choline acetyltransferase and nerve growth factor messenger RNA (Salim, K. N. et al. (2004) "Ginsenoside Rb1 regulates ChAT, NGF and trkA mRNA expression in rat brain," *Brain Res Mol Brain Res* 1997 47:177-182). Other ginsenosides have also been reported to effect specific physiological mechanisms, ginsenoside Rd has been reported to affect corticosterone secretion (Hiai, S. et al. (1983) "Evaluation of corticosterone secretion-inducing activities of ginsenosides and their prosapogenins and sapogenins," *Chem Pharm Bull* (Tokyo) 31(1):168-174) and ginsenosides Rd and Re may inhibit synaptosomal uptake of norepinephrine, dopamine, serotonin and GABA (Tsang, D. et al., (1985) "*Ginseng* saponins influence on neurotransmitter uptake in rat brain synaptosomes," *Planta Med* 47:221-224). Furthermore, in vivo modulation of LTP in the hippocampal formation by Ginsenoside Rb1 has been observed in rats (Abe, K. et al. (1994) "Differential effects of ginsenoside Rb1 and malonylginsenoside Rb1 on long-term potentiation in the dentate gyms of rats," *Brain Res.* 649 (1-2):7-11.)

With respect to evaluating potential cognitive enhancement by whole extract American *Ginseng* (*Panax quinquefolius*), one study observed that scopolamine induced amnesia in Sprague-Dawley rats was attenuated by administration of American *Ginseng*. American *Ginseng* attenuated the scopolamine-associated decrement on performance of the Morris water maze task (spatial learning) and increased choline uptake in synaptosomal preparations (Sloley, B. D., et al. (1999) "American *Ginseng* extract reduces scopolamine induced amnesia in a spatial learning task," *J Psychiatry Neurosci* 24:442-452). However, studies assessing the psychogenic benefits of American *Ginseng* are rare.

SUMMARY OF THE INVENTION

Until now, the beneficial effects of American *Ginseng* on cognitive function have not been known. The present invention provides methods of using American *Ginseng* to enhance cognitive function—including, improvement of working memory, attention, and calmness, among others. The inventors have discovered that administering American *Ginseng* improves working memory (WM) performance: spatial span was improved by all doses at all testing times; other WM tasks were differentially improved by the 200 mg dose (with time- and task-specific benefits associated with other doses). Also, attentional performance (Choice Reaction Time accuracy) was significantly improved by 100 mg at all times and by 200 and 400 mg after 6 h. Furthermore, the 100 mg dose was associated with significantly enhanced "calmness" at 3 h and 6 h.

BRIEF DESCRIPTION OF THE DRAWINGS

Further features, advantages and characteristics of the present invention will become apparent to a person of ordinary skill in the art in view of the following detailed discussion of preferred embodiments of the present invention, made with reference to the drawings annexed, in which.

DETAILED DESCRIPTION OF THE INVENTION

Figure 1:
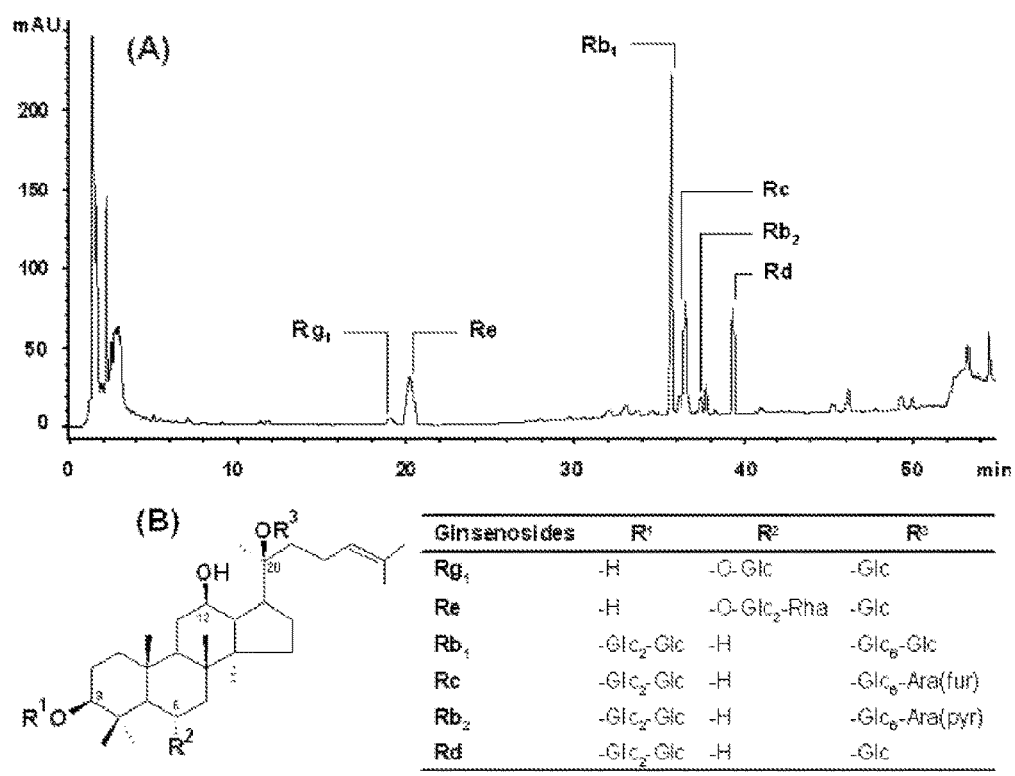
FIG. 1 illustrates: (A) Chromatogram of the American ginseng (*Panax quinquefolius*) extract; and (B) Structures of ginsenosides.

The present invention relates to the novel discovery that acute consumption of *Panax quinquefolius* (American *Ginseng*) can improve cognitive performance, treat anxiety, and increase calmness in healthy young adults. All doses of *Panax quinquefolius* were found to improve some aspect of cognition.

In addition to being administered whole, American *Ginseng* can be administered as an extract, powder, or in other modified form. Based on the modifications, the amount of ginsenosides present may vary. For example, Naturex produces milled root form of American *Ginseng* (Pure Powder), which contains total ginsenosides content between about 3 and 7% (usually standardized to 5%). Naturex also produces an extract of American *Ginseng*, which contains total ginsenosides content between amount 7 to 16% (usually standardized to 10%). The distribution of ginsenosides is similar in all products and a person of ordinary skill in the art would understand how to make other powders, extracts, and modified products containing ginsenosides. The composition described below in connection with a preferred embodiment of the present invention is an extract of American *Ginseng* containing 11.65% of total ginsenosides.

In a preferred embodiment of the invention, the American *Ginseng* extract comprises, by weight of the American *Ginseng* extract, about 0.2% of ginsenoside Rb2 and about 5.0% of ginsenoside Rb1.

In a class of this embodiment, the American *Ginseng* extract further comprises, by weight of the American *Ginseng* extract, about 0.2% of ginsenoside Rg1, about 2.0% of ginsenoside Re, about 2.0% of ginsenoside Rc, and about 1.4% of ginsenoside Rd.

American *Ginseng* can be administered in a range of doses, which can benefit different domains of cognitive function. All doses appeared have some cognitive effects with optimal doses appearing to have some task-specificity. Perhaps the most striking and surprising result was that all three doses improved Corsi block performance compared to placebo at all post-dose time points with the most beneficial effects being observed for the lower two doses. A preferred embodiment of the present invention involves improving Immediate Word Recall accuracy and Numeric Working Memory speed by administering a 200 mg dose. Another preferred embodiment involves improving Alphabetic Working Memory speed by administering 100 mg or 400 mg doses. Another preferred embodiment involves improving Choice Reaction Time accuracy by administering a 100 mg or 400 mg dose 1 hour in advance of desired results. A further preferred embodiment for improving Choice Reaction Time involves administering 100 mg at least 3 hours before desired results, and further preferred to be administered 6 hours before desired results.

For improving Immediate Word Recall and Numeric Working Memory, preferred embodiments involve a dose of 200 mg. For other tasks (Choice Reaction Time, Alphabetic Working Memory and the Corsi block task) both high and low dosages appeared to improve performance. It is further preferred that the American *Ginseng* be administered 6 hours in advance of desired results. As used herein, the term "high dose" refers to a dosage of between 400 and 500 mg, and the term "low dose" refers to a dosage of between 50 and 400 mg.

American *Ginseng* also has beneficial effects on mood in healthy young adults. For example, 100 mg of *Panax quinquefolius* improves feelings of calmness in a time dependent manner. This effect was significantly higher 3 h and 6 h following administration compared to placebo. In contrast, a number of studies have assessed the effect of Asian *Ginseng* (*Panax ginseng*) on mood using the Bond Lader mood scale (Kennedy et al. 2001a; Kennedy et al. 2001b; Kennedy et al. 2002a; Kennedy et al. 2003; Scholey & Kennedy 2002), the same scale used in connection with the present invention. These studies all assessed the acute effects of Asian *Ginseng* on mood. One study demonstrated an effect of Asian *Ginseng* on mood in that at 200 and 400 mg dosages feelings of alertness declined 6-hours following treatment of Asian *Ginseng* (Kennedy et al. 2001a).

Another study assessed the effects of acute administration of Asian *Ginseng* on fatigue in healthy young individuals (Reay et al., 2005) and observed that subjective feelings of mental fatigue were ameliorated in a time-dependent manner by 200 mg *Ginseng* during sustained intense cognitive processing. (The present invention found that self-rated calmness was reduced over the course of testing following placebo and 100 mg American *Ginseng* extract essentially produced increased feeling of calmness, possibly tapping into feelings of fatigue which increased with cognitive testing and were stabilized by 100 mg treatment.) It may be that effects were most pronounced at the later time point due to increasing stress levels over the testing phase, in which case we might attribute an adaptogenic effect might be attributed to the *ginseng* extract. Previous research in rodents has shown that *Ginseng* saponins and Ginsenoside Rb1 inhibit the stress-induced increases in plasma corticosterone (Kim, H. S. et al. (1998) "Effects of ginsenosides on $Ca^{2+}$ channels and membrane capacitance in rat adrenal chromaffin cells," *Brain Res Bull.* 46(3):245-51.)

The present invention relates to the enhancement effects of American *Ginseng* (*Panax quinquefolius*) predominantly on working memory (WM) processes (Corsi block, and both Numeric and Alphabetic Working Memory). This also related to positive effects on short-term verbal declarative memory (Immediate Word Recall) and attention (Choice Reaction Time). WM and short-term memory systems are thought be localized to hippocampal and pre-frontal cortices. It is generally agreed that the hippocampus has an important role in the formation of new memories about experienced events such as episodic or autobiographical memory. While the prefrontal cortex deals with higher-order working memory/executive functions including manipulating working memory (Gabrieli, J. D. (1998) "The role of left prefrontal cortex in language and memory," *Proc Natl Acad Sci USA* 95:906-913; Goldman-Rakic, P. S. (1996) "The prefrontal landscape: Implications of functional architecture for understanding human mentation and the central executive [and discussion]," *Philosophical Transactions of the Royal Society of London, Series B: Biological Sciences* 351:1443-1453), it has been well documented that the cholinergic pathways projecting to the cerebral cortex and hippocampus play a key role in learning and memory and it has been argued that the brain cholinergic system is a specific target for cognitively enhancing agents (Giovannini, M. G. et al. (1995) "Differential regulation by N-methyl-D-aspartate and non-N-methyl-D-aspartate receptors of acetylcholine release from the rat striatum in vivo," *Neuroscience* 65(2):409-15.) A number of studies have identified cholinergic properties associated with isolated ginsenosides. A direct interaction between Rg2 and nicotinic receptor subtypes has been observed (Sala, F. et al. (2002) "Effects of ginsenoside Rg2 on human neuronal nicotinic acetylcholine receptors," *J Pharmacol Exp Ther.* 301(3):1052-59.) Moreover Benishin (1992) demonstrated modulation by Rb1 of acetylcholine release and reuptake, along with a number of choline uptake sites in the hippocampus, and to a lesser extent, the cortex. Both ginsenosides Rg1 (Zhang et al. 1990) and Rb1 (Salim et al. 2004; Zhang et al. 1990) have also been shown to increase choline acetyltransferase levels in rodent brains.

In animal research, one study observed that scopolamine-induced deficits are attenuated by American Ginseng (*Panax quinquefolius*) in Sprague Dawley rats (Sloley et al. 1999). Protection against scopolamine-induced amnesia by American *Ginseng* was most evident in trials where animals were required to remember the task learned the previous day. In this study it was also observed that American *Ginseng* increased choline uptake into synaptosomes prepared from rat brain. Also, in the human brain crude extracts of Asian *Ginseng* exhibited an affinity for both nicotinic and muscarinic receptors in cerebral cortex membranes, (Lewis, R. et al., "Non-ginsenoside nicotinic activity in *ginseng* species," *Phytother Res.* 13(1):59-64.)

As discussed previously, the American *Ginseng* extract profile has 2-3 times the ginsenoside content than the more commonly researched Asian *Ginseng*, with the highest expression of Rb1 and Re. The cholinergic system is one potential central mechanism of action on the enhancement of memory by American *Ginseng*.

The inventors also assessed the acute effects of American *Ginseng* (*Panax quinquefolius*) on glucoregulation on young healthy adults. Vuksan et al. (2000) previously observed that 300 mg *Panax quinquefolius* lowered blood glucose levels during a glucose challenge in both healthy and diabetic subjects. (Vuksan, V. et al. (2000a) "American *ginseng* (*Panax quinquefolius* L) reduces postprandial glycemia in nondiabetic subjects and subjects with type 2 diabetes mellitus," *Arch Intern Med.* 160(7):1009-13.) Other studies also observed similar results: American *Ginseng* appeared to have significant hypoglycemic action in rodents (Oshima, Y. et al. (1987) "Isolation and hypoglycemic activity of quinquefolans A, B, and C, glycans of *Panax* quinquefolium roots," *J Nat Prod* 50:188-190; Martinez, B. & Staba, E. J. (1984) "The physiological effects of *Aralia, Panax* and *Eleutherococcus* on exercised rats," *Jpn J Pharmacol* 35:79-85). In humans, American *Ginseng* also reduced blood glucose levels following a 25-g glucose challenge in both diabetic patients who had ingested 300, 600, and 900 mg and non diabetics administered 100, 200, and 300 mg (Vuksan, V. et al., 2000a; Vuksan, V. et al. (2000b) "Similar postprandial glycemic reductions with escalation of dose and administration time of American *Ginseng* in type 2 diabetes," *Diabetes Care* 23:1221-1226; Vuksan, V. (2006) "Korean red *Ginseng* (*Panax Ginseng*) improves glucose and insulin regulation in well controlled type 2 diabetes: results of a randomized, double-blind, placebo-controlled study of efficacy and safety," *Nutr Metab Cardiovasc Dis* 18:46-56) (Vuksan et al. 2000a). The present invention, however, shows that, at least at the dosages used here (100 mg, 200 mg, and 400 mg), American *Ginseng* has no detectable effect on blood glucose levels.

Overall the present invention is the first to demonstrate cognitive and mood enhancement following *Panax quinquefolius* administration. Cognition-enhancing effects of the present invention were observed across a range of cognitive modalities at a range of dosages. The lack of glycaemic effects also highlights important methodological differences between existing literature and the present invention, and thus one of ordinary skill in the art will more fully understand how American *Ginseng*'s impact on glucose levels may be moderated.

EXAMPLES

The results of each of the following examples were tested by a randomized, double-blind, placebo-controlled, crossover trial (N=32 healthy young adults) to evaluate the acute mood, neurocognitive and blood glucose effects of 3 doses (100, 200, 400 mg) of an American *ginseng* extract (standardized to 10.65% ginsenosides) compared to placebo. On study days (separated by a >7-day wash-out) participants underwent a baseline assessment of mood, cognitive function and blood glucose. They then took the day's treatment followed by the same assessments 1, 3 and 6 hours later. Statistical analysis used a two-way (Treatment×Time) ANOVA followed by pre-planned comparisons of each dose's effects compared with placebo at each time point.

Participants

Thirty two participants (16 male, 16 female) were recruited via advertisements in local newspapers and university bulletin boards to take part in the study. Ages ranged from 18 to 40 years (M=25.2, SD=4.97). All participants reported that they were in good health, not taking any drugs or medications (excluding the contraceptive pill), had no known food allergies and were non smokers.

They completed an initial health screening questionnaire which excluded participants with a number of medical conditions (e.g. diabetes, hypoglycemia, psychiatric disorders, epilepsy, and gastrointestinal disorders) or who were on prescribed medications, were pregnant or lactating. They were advised to refrain from taking any vitamins, other herbal supplements and over the counter medicines for the whole period of study. On the testing days, participants were advised to abstain from consuming alcohol, caffeine products and energy drinks They were required to eat a light breakfast (toast or cereal) at least 2 hours before the onset of the experiment and were provided with sandwich for lunch (with either chicken and salad, or cheese and salad). The study was approved by the Swinburne University Human Research Ethics Committee and all participants gave written informed consent. The study was conducted according to the Declaration of Helsinki Volunteers received a 200 AUD cheque at the end of the study for their participation.

Treatments

The coated capsules utilized in the study contained a standardized to 10% Ginsenosides commercial extract of *Panax quinquefolius* (American *Ginseng*) prepared and provided by Naturex.

Extract Preparation

The roots of American *ginseng* (*Panax quinquefolius*) were authenticated using macroscopic, microscopic, and high performance thin layer chromatography techniques (Reich, E. & Schibli (2007) "A In: High-Performance Thin-Layer Chromatography for the Analysis of Medicinal Plants," ISBN: 9781588904096, Thieme Medical Publishers Inc., New York, N.Y.). The American *ginseng* extract was obtained through an industrial process (Naturex, USA, Reference: 331350, Lot number: E15/05/D8). First, the *ginseng* roots were ground to be between ¼ and ½ inch, and then the ground roots were soaked three times during five hour intervals in an ethanol/water (75/25, v/v) solution at 40° C. After filtration, the clarified solution was then concentrated under vacuum at 45° C. The three pools were combined and concentrated again until the total solids on dry basis were around 60%. This is the Native Extract, which was then mixed with maltodextrin as a carrier and spray dried to obtain a fine powder. The moisture content in the extract was less than 5%. After extraction, the sample was analyzed for its content of pesticides (USP. General Chapters: <561>

Articles of Botanical Origin. Test for Pesticides. USP-31-NF26 S1, Rockville, Md. 2008) and heavy metals (method 993.14, AOAC, Official Methods of Analysis (2005) 18th Ed. AOAC International, Gaithersburg, Md.) at Covance Laboratories (Madison, Wis., USA) for compliance. The American ginseng extract was found to be below the Maximum Residue Limits established for pesticides and heavy metals (Durgnat, J. M. et al. (2005) "Quality and safety assessment of ginseng extracts by determination of the contents of pesticides and metals," Food Additives & Contaminants 22:1224-1230).

The American ginseng extract used in this clinical trial contained 0.28% of Rg1, 2.06% of Re, 5.69% of Rb1, 1.87% of Rc, 0.29% of Rb2, and 1.48% of Rd. The total ginsenosides, calculated as the sum of above individual ginsenosides, represented 11.65% in the American ginseng extract. As expected, the ginsenoside Rf was not found (Harkey, M. R. et al. (2001) "Variability in commercial ginseng products: an analysis of 25 preparations," Am J Clin Nut 73:1101-1106). The ginsenoside Rf is not present in American ginseng but it is present in Asian ginseng (Panax ginseng), and is used as a marker to determine adulterations in American ginseng. The chromatogram of the American ginseng extract and the structures of its ginsenosides is presented in FIG. 1.

Initial one-way analyses on each cognitive and mood measure revealed no significant baseline differences between conditions confirming that post-treatment effects were not attributable to change differences in baseline performance. Significant effects associated with treatments are presented in FIG. 2.

Example 1

Administering American Ginseng served to improve Choice Reaction Time in the following situation.

Choice Reaction Time: The arrow pointing to the left or right was presented in the centre of the screen at irregular time intervals. The volunteer makes a response with 'left' and 'right' cursor buttons to arrows pointing to the left or right respectively as quickly as possible. Each of the 15 stimuli remained on screen until the key press was registered. The inter-stimulus interval randomly varying between 1 and 3 seconds. Outcomes were accuracy (% correct) and reaction time (ms).

Four Choice Reaction Time: A replica of the four direction arrow keys found at the bottom and to the right of the computer keyboard appeared on the screen. The participants were instructed to make a response as quickly and as accurately as possible with 'left', 'right', 'up' and 'down' cursor keys corresponding to the arrow being illuminated on the screen one at a time, pointing randomly to the left, right, up or down. Each of the 16 stimuli remained on screen until the key press was registered. The inter-stimulus interval randomly varying between 1 and 3 seconds. The task was scored for accuracy (% correct) and reaction time (ms).

For Choice Reaction Time accuracy there was a significant main effect of treatment [$F(3,162)=3.406$, $p=0.021$). Comparisons of each dose at each time point revealed significant improvements associated with the 100 mg dose at all three time points. There were also significant improvements for 200 mg at 1 hr and both 200 mg and 100 mg at 6 hrs ($P<0.05$ in all cases).

Example 2

Administering American Ginseng served to improve Immediate Word Recall in the following situation.

Word Presentation: Ten common English words appropriate for the age range of participants were drawn from http://www.math.yorku.ca/SCS/Online/paivio/. Words were matched for linguistic familiarity, concreteness and frequency and presented in sequence on the monitor for the participant to remember at the commencement of the battery. Stimulus duration was 1 s, as was the inter-stimulus interval.

Immediate word recall: The participant was allowed 60 s to write down as many of the retained words as possible. The task was scored for number of correct answers, errors and intrusions and the resulting score was converted into a percentage.

Figure 2:
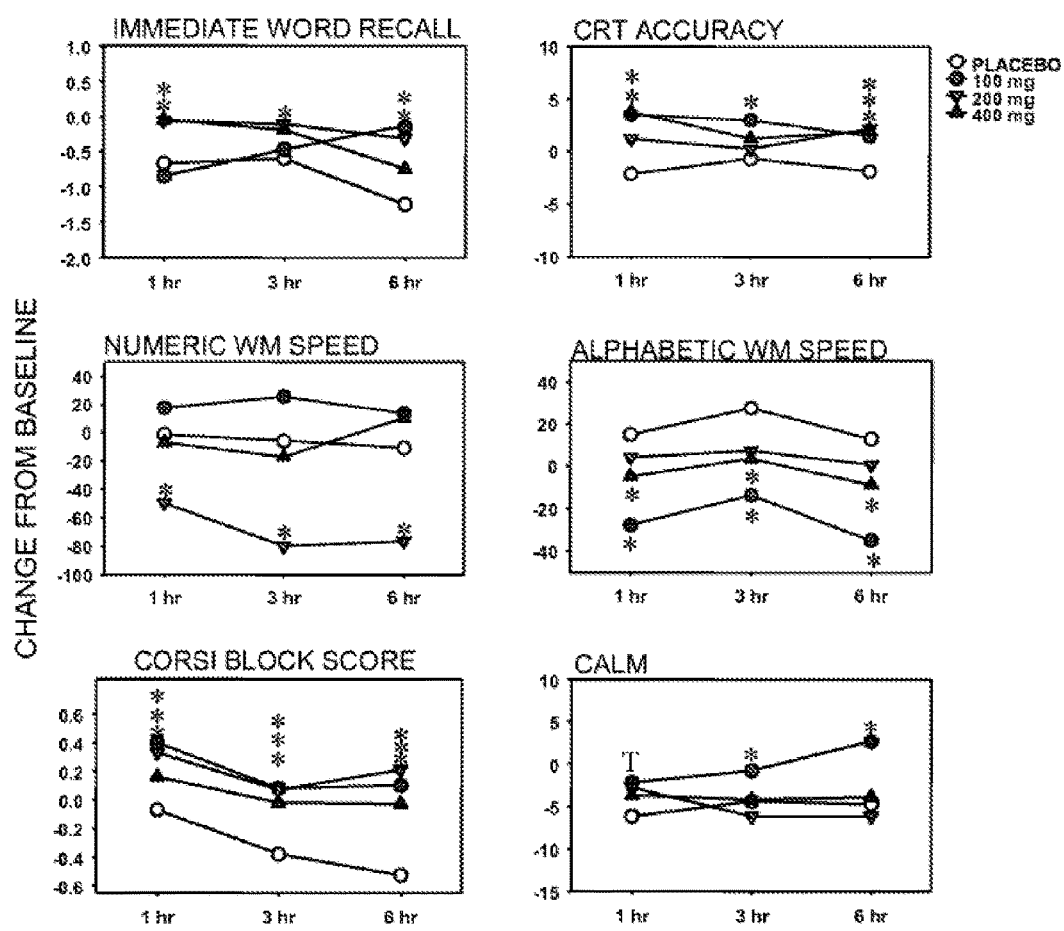
FIG. 2 illustrates the significant effects of *Panax quinquefolius* on cognitive function and mood. Graphs depict mean change-from-baseline scores following a placebo and 100 mg, 200 mg and 400 mg of a standardised extract. Significant differences from placebo at each time point are indicated (*, $p<0.05$)

There was a significant Treatment×Time interaction [$F(6, 174)=2.399$, $p=0.03$)]. Comparisons of each dose at each time point revealed significant improvements associated with the 200 mg dose at all three time points. There were also significant improvements for 400 mg at 1 hr and 100 mg at 6 hr only ($p<0.05$ in all cases). Results are shown in FIG. 2.

Example 3

Administering American Ginseng served to improve Numeric Working Memory speed in the following situation.

Numeric Working Memory: A series of five digits was presented on the computer screen sequentially for the participants to hold in their memory. This is followed by a series of 30 probe digits. The participants decided whether or not the digit was from the original series and indicated their choice by pressing corresponding keys labelled 'YES' and 'NO'. This was repeated three further times with different stimuli sets. Reaction times (ms) and accuracy (% correct) were measured.

There was a significant main effect of Treatment for Numeric Working Memory speed. Comparisons of each dose at each time point revealed significant improvements associated with the 200 mg dose at all three time points. ($p<0.05$ in all cases).

Example 4

Administering American Ginseng improved Alphabetic Working Memory in the following situation.

Alphabetic Working Memory: This was similar to the numeric working memory but using letters. A series of 5 letters appeared on the screen for participant to remember. After 4 seconds the letters disappeared and were followed by a series of 30 probe letters. Participants were instructed to indicate whether the target letter had appeared in the original list of five letters by pressing corresponding 'YES' or 'NO' key as quickly as possible. The measures were the percentage of the correctly identified stimuli and the average reaction time (ms).

There was a trend for a main effect of Treatment for Alphabetic Working Memory [$F(3,60)=2.7$, $p=0.063$]. This trend merited further exploration and comparisons of each dose at each time point revealed significant improvements associated with the 100 mg and 400 mg doses at all three time points ($p<0.05$ in all cases).

Example 5

Administering American Ginseng served to improve spatial span in the following situation.

Corsi Blocks: The Corsi Block-Tapping Task (initially developed by Corsi, 1972) is a span task and a visuospatial analogue to the digit span of verbal short-term memory (Lezak, 1995). A computerized version of the Corsi blocks task was employed in the study. A series of squares appeared on the screen. A number of these illuminated sequentially in quasi-random order. The volunteer then attempted to repeat the pattern by clicking the boxes in the same order with the mouse and cursor. The difficulty increases from 4 blocks upwards. The task gives a measure of spatial span as well as speed of responding.

There was a significant main effects of Treatment on mean Corsi block score [$F(3,114)=2.925$, $p=0.041$]. Comparisons of each dose at each time point revealed significant improvements associated with the all doses at all time points. ($p<0.05$ in all cases).

Example 6

Administering American *Ginseng* served to improve calmness in the following situation.

Depression Anxiety and Stress Scale (DASS; Lovibond & Lovibond, 1995): The shortened 21-item version of the DASS was used to assess three negative affective states of depression, anxiety and stress on seven-item scales. The Depression subscale (DASS-D) measures symptoms relating to dysphoric mood (e.g. sadness), for example "I couldn't seem to experience any positive feeling at all." The Anxiety subscale (DASS-A) assesses symptoms associated with physiological hyperarousal such as autonomic arousal, for example "I felt I was close to panic." The Stress subscale (DASS-S) assesses symptoms associated with nervous arousal, for example "I tended to over-react to situations." Participants were required to indicate on a 4-point scale whether each statement applied to them not at all, to some degree, a considerable degree, or most of the time. Scores were calculated by summing the scores of the appropriate items. Good internal consistency and validity for the DASS have been found with samples of clinical patients and non-clinical volunteers (Anthony et al., 1998).

State-Trait Anxiety Inventory (STAI): The State-Trait Anxiety Inventory (STAI) (Speilberger et al, 1969) comprises two scales. The 'State' (STAI-S) subscale is a widely used instrument for measuring fluctuating levels of anxiety. The subscale contains 20 statements (e.g. 'I am calm'). Participants rate how much they feel like each statement at the time of making the response by marking a 4-point scale ranging from "not at all" to "very much so." The "Trait" (STAI-T) subscale comprises 20 different statements (e.g. "Some unimportant thought runs through my mind and bothers me"). Participants are asked to indicate how they generally feel on a scale ranging from "almost never" to "almost always." Scores on both sections of the STAI range from 20 to 80, with higher scores indicating more anxiety.

Symptom checklist: The symptom checklist consisted of 28 physiological/psychological problems people might have (e.g. I feel dizzy, I have a dry mouth, I feel anxious more than usual). Participants indicated how much the problem had bothered them in the last 7 days including today using a 5-point scale from "not at all" to "very much so."

There was a single significant effect on mood measures. The Treatment×Time interaction on self-rated calmness was significant [$F6, 150=2.345$, $p=0.034$]. Comparisons of each dose at each time point revealed significant improvements associated with the 100 mg dose at 3 h and 6 h only ($p<0.05$ in both cases).

One skilled in the art will appreciate that the present invention can be practiced by other than the embodiments disclosed herein, which are presented for purposes of illustration, and not of limitation.

The invention claimed is:

1. A method of enhancing cognitive performance in working memory of a human subject in need thereof, the method comprising administering to said human subject a composition comprising American *ginseng* extract and a carrier, in an effective amount to enhance the cognitive performance, wherein said American *ginseng* extract comprises, by weight of said American *ginseng* extract, about 0.2% of ginsenoside Rb2 and about 5.0% of ginsenoside Rb1.

2. The method of claim 1, wherein said American *ginseng* extract further comprises, by weight of said American *ginseng* extract, about 0.2% of ginsenoside Rg1, about 2.0% of ginsenoside Re, about 2.0% of ginsenoside Rc, and about 1.4% of ginsenoside Rd.

3. The method of claim 2, wherein said American *ginseng* extract is free of ginsenoside Rf.

4. The method of claim 2, wherein said effective amount comprises about 23.30 mg of said ginsenoside Rb2, said ginsenoside Rg1, said ginsenoside Re, said ginsenoside Rb1, said ginsenoside Rc, and said ginsenoside Rd in total.

5. The method of claim 1, wherein said effective amount is between 100 and 400 mg.

6. The method of claim 1, wherein said carrier is maltodextrin.

7. The method of claim 1, wherein the method further comprises assessing said cognitive performance by administering a test to said human subject, said test is Corsi block task, Numeric Working Memory test, Alphabetic Working Memory test, or a mixture thereof.

8. The method of claim 7, wherein said human subject is administered said composition between 1 and 6 hours prior to the step of assessing said cognitive performance.

* * * * *